United States Patent [19]

Schäfer

[11] Patent Number: 6,166,222
[45] Date of Patent: Dec. 26, 2000

[54] METHOD FOR PRODUCING CHIRAL 3,4-DEHYDROPROLINES

[75] Inventor: Bernd Schäfer, Dierbach, Germany

[73] Assignee: BASF Aktiengesellschaft, Ludwigshafen, Germany

[21] Appl. No.: 09/424,933

[22] PCT Filed: Jun. 2, 1998

[86] PCT No.: PCT/EP98/03284

§ 371 Date: Dec. 1, 1999

§ 102(e) Date: Dec. 1, 1999

[87] PCT Pub. No.: WO98/55456

PCT Pub. Date: Dec. 10, 1998

[30] Foreign Application Priority Data

Jun. 4, 1997 [DE] Germany .......................... 197 23 473

[51] Int. Cl.[7] ....................... C07D 207/18; C07D 207/24
[52] U.S. Cl. ..................... 548/530; 548/406; 548/539; 548/565
[58] Field of Search ................................. 548/530, 539, 548/565, 406

[56] References Cited

FOREIGN PATENT DOCUMENTS

| 19630082 | 1/1998 | Germany . |
| 98/04523 | 2/1998 | WIPO . |

OTHER PUBLICATIONS

Donohoe et al., *J. Org. Chem.*, 1996, 61, 7664–7665.
Donohoe et al., *J. Chem. Soc. Perkin Trans.*, 1998, 667–676.
Jones et al., *Tetrahedron Letters*, 36(37), 1995, 6743–44.

*Primary Examiner*—Joseph K. McKane
*Assistant Examiner*—Jane C. Osweeki
*Attorney, Agent, or Firm*—Keil & Weinkauf

[57] ABSTRACT

The invention relates to a process for preparing chiral 3,4-dehydroproline compounds of formula (I), in which R, R' and R" have the meanings given in the description. The invention is characterized by a pyrrolecarboxylic acid derivative compound of formula (II) reacted first with an alkali or alkaline earth metal in ammonia and then with an aqueous salt solution or a compound of formula (III) in which X is a leaving group to form the final chiral product compound.

5 Claims, No Drawings

METHOD FOR PRODUCING CHIRAL 3,4-DEHYDROPROLINES

This application is a 371 of PCT/EP98/03284 filed Jun. 2, 1998.

The present invention relates to a process for preparing chiral 3,4-dehydroprolines.

Chiral 3,4-dehydroprolines are prepared starting from 4-hydroxyproline by a Chugaev reaction (P. Grogg, Angew. Chem. 92 (1980) 761). Besides yields which are comparatively poor (64%), this method requires the use of highly toxic compounds such as carbon disulfide, methyl iodide and methyl mercaptan. The pyrolytic decomposition at 180–190° C. and 12 Torr requires great industrial expenditure.

It is also possible in place of the xanthates to convert the corresponding iodides, sulfoxides or selenoxides by thermolysis (J.-R. Dormoy, Synthesis (1982) 752). However, this does not solve the fundamental problems of toxicity and industrial expenditure.

Achiral syntheses normally start from pyrrolecarboxylic acid, which is reduced with phosphonium iodide/hydrogen iodide (J. W. Scott, Synth. Commun. 10 (1980) 529). The racemate is then resolved by crystallization with chiral amines (S. S. Kerwar, J. Biol. Chem. 251 (1976) 503; U.S. Pat. No. 4,066,658) or tartaric acid (A. Corbella, Chem. Ind. (1969) 583). The disadvantage of this synthesis is the use of the highly toxic phosphine and a maximum yield of 50% in the racemate resolution.

German Patent Application 19630082.7, which is not a prior publication, describes the elimination of sulfonic esters of hydroxyproline ester and subsequent enzymatic racemate resolution. The elimination is associated with racemization of the center of asymmetry of the proline. The maximum yield possible in principle in both the classical and the enzymatic racemate resolutions is 50%. This can be improved by recycling the unresolved enantiomer only with considerable expenditure.

Alkylating asymmetric Birch reductions are described by A. G. Schultz (J. Am. Chem. Soc. 110 (1988) 7828) on benzoic acid derivatives and by T. Kinoshita (J. Heterocycl. Chem. 33 (1996) 1313) on furancarboxylic acid derivatives.

Birch reduction of pyrrole derivatives was unknown until recently. T. J. Donohoe was the first to describe, in J. Org. Chem. 61 (1996) 7664, the achiral Birch reduction of pyrrole-2-carboxylic acid derivatives. To date, it has been possible to resolve these into the enantiomers only by classical or enzymatic racemate resolution.

We have now found that chiral 3,4-dehydroprolines can be obtained by diastereoselective Birch reduction.

The invention relates to a process for preparing chiral 3,4-dehydroprolines of the formula I

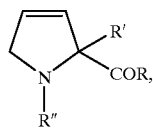

I where
  R is a chiral group,
  R' is hydrogen or a $C_{1-6}$-alkyl, $C_{2-7}$-alkenyl, $C_{7-9}$-arylalkyl or tri-$C_{1-4}$-alkylsilyl radical and
  R'' is a protective group
which comprises reacting a pyrrolecarboxylic acid derivative of the formula II

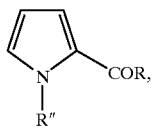

II in ammonia with an alkali metal or alkaline earth metal and then with an aqueous salt solution or a compound of the formula III

R'—X    III, where X is a leaving group.

Particularly suitable sources of the chiral groups R are nonaromatic chiral secondary amines and nonaromatic chiral alcohols of the formula RH. Specific mention may be made of the following

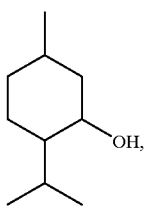

A

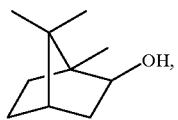

B

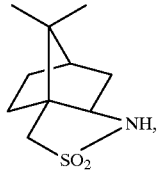

C

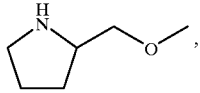

D

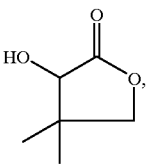

E

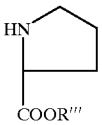

F

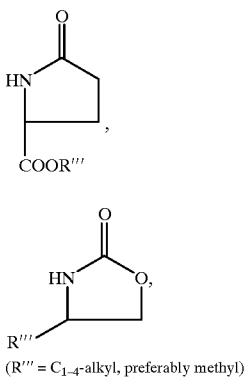

(R''' = C$_{1-4}$-alkyl, preferably methyl)

Of these, compound D is particularly preferred.

R' is preferably hydrogen, C$_{1-3}$-alkyl, allyl or benzyl. A tri-C$_{1-4}$-alkylsilyl radical which should be particularly mentioned is the trimethylsilyl radical.

Protective groups which should be mentioned for R" are Boc, C$_{1-6}$-acyl, mesyl, benzenesulfonyl and tosyl, and preferably Boc.

Preferred leaving groups for X are Cl, Br, I, MesO, TosO or triflate.

Alkali metals and alkaline earth metals which should be mentioned for the reaction are magnesium and, especially, lithium, sodium and potassium. The reaction takes place in liquid or supercritical ammonia, to which an inert solvent may also be added. Preferred solvents are THF and C$_{1-6}$-alcohols.

The reaction is generally carried out at a temperature in the range from −100 to +100° C. and under a pressure in the range from 1 to 200 bar. The boiling point of the reaction mixture and 1 bar are preferred. A reaction under autogenous pressure is very particularly preferred.

The reaction is complete when pyrrole derivatives are no longer detectable in the reaction mixture (eg. by GC, HPLC, TLC).

Workup to product is, as a rule, carried out by conventional processes such as distillation, filtration, centrifugation or extraction.

The novel process can be carried out batchwise, eg. in a stirred reactor. However, the simplicity of the procedure has the advantage that the reaction can also be carried out continuously, for example using a reaction tube or a cascade of stirred reactors.

The resulting crude products can, if desired, be purified further, eg. by crystallization, extraction or chromatography.

It is surprising that pyrrole-2-carboxylic esters and -carboxamides can, despite the sterically demanding and electronically diverse chiral groups, be converted into the corresponding dehydroprolines in some cases with very high selectivities. It is particularly surprising in this connection that this applies not only to the alkylation but also to the protolysis of the reaction intermediate.

The chiral 3,4-dehydroprolines of the formula I which can be prepared straightforwardly by the novel process are valuable intermediates for synthesizing dyes, crop protection agents or drugs, in particular thrombin inhibitors as described, for example, in the publication PCT/WO 9625426.

EXAMPLE 1

Synthesis of N-Boc-3,4-dehydroproline (S)-2-methoxymethylpyrrolidinide 150 ml of ammonia and 50 ml of THF were mixed at −30° C. Then 0.42 g (0.06 mol) of lithium was added. 6.17 g (0.02 mol) of N-Boc-pyrrole-2-carboxylic acid (S)-2-methoxymethylpyrrolidinide dissolved in 20 ml of THF were added dropwise to this mixture over the course of 5 min. After subsequent stirring for 1 h, 10 ml of saturated ammonium chloride solution and 150 ml of saturated sodium chloride solution were added, the phases were separated and the aqueous phase was extracted three times with 50 ml of dichloromethane each time. The organic phases combined and concentrated. 4.8 g (0.015 mol, 77%) of the product were obtained in the form of a yellowish red oil. $^1$H-NMR (δ, ppm, d6-DMSO , T=373K): 1.38 (1s, integral: 95:5, t-butyl).

EXAMPLE 2

Synthesis of N-Boc-3,4-dehydroproline (1S)-endo-bornyl ester 150 ml of ammonia and 50 ml of THF were mixed at −30° C. Then 0.24 g (0.034 mol) of lithium was added. 4 g (0.0115 mol) of (IS)-endo-bornyl N-Boc-pyrrole-2-carboxylate dissolved in 10 ml of THF were added dropwise to this mixture over the course of 5 min. After subsequent stirring for 1 h, 2 ml of saturated ammonium chloride solution and 150 ml of saturated sodium chloride solution were added, the phases were separated and the aqueous phase was extracted three times with 100 ml of dichloromethane each time. The organic phases were combined, dried over sodium sulfate and concentrated. Yield: 3.2 g (0.009 mol, 61%). $^1$H-NMR (δ, ppm, d6-DMSO, T=358K): 1.4 (2s, integral: 57:96, t-butyl).

EXAMPLE 3

Synthesis of N-Boc-3,4-dehydroproline (1R,2S,5R)-menthyl ester 0.58 g (0.084 mol) of lithium was added to 100 ml of ammonia and 23 ml of THF at −30° C. 10 g (0.028 mol) of (1R,2S,5R)-menthyl N-Boc-pyrrole-2-carboxylate dissolved in 20 ml of THF were added dropwise to this mixture. After stirring for 1 h, 5g of ammonium chloride, 100 ml of THF and 7.5 g of Celite® were added, and the ammonia was allowed to evaporate. The suspension was filtered, and the filtrate was concentrated. Yield: 8.4 g (0.024 mol, 85%). $^1$H-NMR (δ, ppm, CDCl$_3$): 1.325–1.425 (each 2s, integral: 67:92, t-butyl).

EXAMPLE 4

Synthesis of N-Boc-3,4-dehydroproline (1S)-2,10-camphorsulfamide 0.15 g (0.023 mol) of lithium was added to 100 ml of ammonia and 50 ml of THF at −70° C. 3.2 g (0.0078 mol) of N-Boc-pyrrole-2-carboxylic acid (1S)-2,10-camphorsulfamide [sic] dissolved in 20 ml of THF were added dropwise to this mixture. After stirring for 1 h, 4 g of ammonium chloride, 25 ml of THF and 3 g of Celite® were added, and the ammonia was allowed to evaporate. The suspension was filtered, and the filtrate was concentrated. Yield: 4 g (still contains LiCl). $^1$H-NMR (δ, ppm, CDCl$_3$: 1.37–1.46 (each 2s, integral 69:30, t-butyl).

What is claimed is:

1. A process for preparing chiral 3,4-dehydroprolines of the formula I

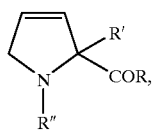
I where
R is a chiral group,
R' is hydrogen or a $C_1$–$C_6$-alkyl, $C_{2-7}$-alkenyl, $C_{7-9}$-arylalkyl or tri-$C_{1-4}$-alkylsilyl radical and
R" is a protective group,
which comprises reacting a pyrrolecarboxylic acid derivative of the formula II

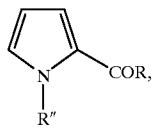
II in ammonia with an alkali metal or alkaline earth metal and then with an aqueous salt solution or a compound of the formula III

R'—X                III, where X is a leaving group.

2. A process as claimed in claim 1, wherein R is the radical of a chiral amine or of a chiral alcohol.

3. A process as claimed in claim 2, wherein R is an enantiomeric or diastereomeric form of any one of the following compounds:

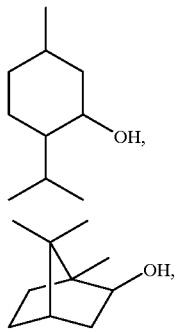

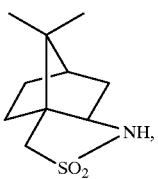

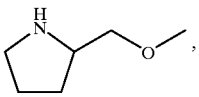

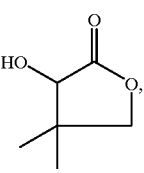
E

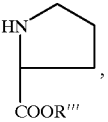
F

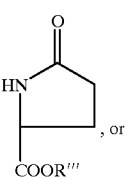
G

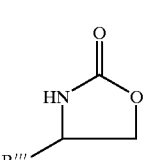
, or

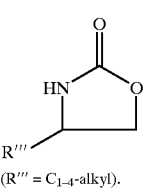
I ($R''' = C_{1-4}$-alkyl).

4. A process as claimed in claim 1, wherein the reaction is carried out in the presence of an inert solvent.

5. A process as claimed in claim 1, wherein the reaction is carried out under a pressure in the range from 1 to 200 bar and at from −100 to +100° C.

* * * * *